(12) United States Patent
Porcs-Makkay et al.

(10) Patent No.: US 7,960,558 B2
(45) Date of Patent: Jun. 14, 2011

(54) PHARMACEUTICAL INTERMEDIATE FOR SYNTHESIZING ACE INHIBITORS AND THE USE THEREOF

(75) Inventors: Márta Porcs-Makkay, Pomáz (HU); Gyula Simig, Budapest (HU); Tibor Mezei, Budapest (HU); Angéla Veressné Pandur, Mende (HU); Gyula Lukács, Budapest (HU)

(73) Assignee: Egis Gyogyszergyar Nyilvanosan Mukodo Reszvenytarsasag, Budapest (HU)

( * ) Notice: Subject to any disclaimer, the term of this patent is extended or adjusted under 35 U.S.C. 154(b) by 96 days.

(21) Appl. No.: 12/300,545

(22) PCT Filed: May 11, 2007

(86) PCT No.: PCT/HU2007/000039
§ 371 (c)(1),
(2), (4) Date: Apr. 30, 2009

(87) PCT Pub. No.: WO2007/132277
PCT Pub. Date: Nov. 22, 2007

(65) Prior Publication Data
US 2010/0286404 A1 Nov. 11, 2010

(30) Foreign Application Priority Data

May 12, 2006 (HU) .................................. 0600403
May 12, 2006 (HU) .................................. 0600404

(51) Int. Cl.
*C07D 263/44* (2006.01)
*C07D 209/52* (2006.01)
*C07D 209/42* (2006.01)
*C07C 69/96* (2006.01)

(52) U.S. Cl. ......... 548/226; 548/452; 548/493; 558/263
(58) Field of Classification Search ................ 548/226, 548/452, 493; 558/263
See application file for complete search history.

(56) References Cited

U.S. PATENT DOCUMENTS

| 2,644,808 A | 7/1953 | Brubaker et al. ............... 260/78 |
| 4,496,541 A | 1/1985 | Huang et al. ..................... 514/2 |
| 4,686,295 A | 8/1987 | Youssefyeh et al. .......... 548/226 |
| 4,716,235 A | 12/1987 | Takahashi et al. ............. 548/533 |
| 5,359,086 A | 10/1994 | Merslavic et al. ............. 548/533 |
| 6,262,274 B1 | 7/2001 | Chen et al. ..................... 548/227 |
| 2004/0248814 A1 | 12/2004 | Cid ................................. 514/19 |
| 2007/0197821 A1 | 8/2007 | Simig et al. ................... 560/159 |

*Primary Examiner* — Kamal A Saeed
*Assistant Examiner* — Kristin Bianchi
(74) *Attorney, Agent, or Firm* — Jonathan Myers; Andrew Wilford (57) ABSTRACT

The compounds of the general Formula (I), wherein $R^1$ is aryl or alkyl; $R^2$ represents alkyl; $R^3$ represents alkyl or aralkyl, are valuable pharmaceutical intermediates, which can be prepared by reacting a compound of the general Formula (IV) (wherein the definitions of $R^1$ and $R^2$ are as above), with at least 2 molar equivalents of the compound of the general Formula (VI) (wherein X represents halogen or tertiary butyloxycarbonyloxy group and $R^3$ is as defined above). The known compounds of the general Formula (II) (wherein $R^1$ and $R^2$ are as defined above) are prepared by reacting the compounds of the general Formula (I) with thionyl chloride. The compounds of the general Formula (I) are new intermediates useful in the synthesis of pharmaceutically active ingredients, particularly in the preparation of ACE-inhibitors, e.g. enalapril, perindopril or ramipril.

26 Claims, 4 Drawing Sheets

Fig. 1
Reaction Scheme 1

Fig. 2

Reaction Scheme 2

Fig. 3

Reaction Scheme 3

Fig. 4

Reaction Scheme 4

PHARMACEUTICAL INTERMEDIATE FOR SYNTHESIZING ACE INHIBITORS AND THE USE THEREOF

CROSS REFERENCE TO RELATED APPLICATIONS

This application is the U.S. national phase of PCT application PCT/HU2007/000039, filed 11 May 2007, published 22Nov. 2008 as WO2007/132277, and claiming the priority of Hungarian patent application P0600403 itself filed 12 May 2006 and PCT patent application PCT/HU2007/000039 itself filed 11 May 2007, whose entire disclosures are herewith incorporated by reference.

FIELD OF THE INVENTION

The present invention relates to new pharmaceutical intermediates and to their use. More specifically, the present invention is concerned with new intermediates useful in the manufacture of pharmaceutical products, particularly in the synthesis of ACE-inhibitors, a process for preparation thereof and a process for the conversion of said intermediates into pharmaceutically active ingredients, especially into ACE-inhibitors.

According to an aspect of the present invention, there are provided compounds of the general Formula (I), (I)

wherein
$R^1$ is aryl or alkyl;
$R^2$ is an alkyl; and
$R^3$ is alkyl or aralkyl.

According to a further aspect of the present invention there is provided a process for the preparation of the compounds of general Formula (I), (wherein the meaning of $R^1$, $R^2$ and $R^3$ is as stated above), which comprises reacting a compound of the general Formula (IV),

(IV)

(wherein the meaning of $R^1$ and $R^2$ is as defined above) with at least 2 molar equivalents of a compound of the general Formula (VI)

XCOOR$^3$ (VI)

(wherein X represents a halogen atom or a tertiary butoxycarbonyloxy moiety and the meaning of $R^3$ is the same as defined above), in an organic solvent as reaction medium and in the presence of an acid-binding agent.

According to a still further aspect of the present invention there is provided a process for the preparation of the compounds of the general Formula (II)

(II)

(wherein the meaning of $R^1$ and $R^2$ is as defined in claim 1), which comprises reacting a compound of the general Formula (I) (wherein the meaning of $R^1$, $R^2$ and $R^3$ is as defined in claim 1), in an organic solvent with thionyl chloride.

According to a still further aspect of the present invention, there is provided a process for the preparation of the compounds of the general Formula (II) (wherein the meaning of $R^1$ and $R^2$ is as defined in claim 1), which comprises reacting a compound of the general Formula (IV) (wherein the meaning of $R^1$ and $R^2$ are as defined above), in an organic solvent in the presence of an acid-binding agent with at least 2 molar equivalents of a compound of the general Formula (VI) (wherein the meaning of $R^3$ and X is as stated above), thereafter reacting the compound of the general Formula (I) thus obtained in an organic solvent with thionyl chloride.

According to a further aspect of the present invention there is provided a process for the preparation of a compound of the general Formula (III)

(III)

wherein $R^1$ is aryl or alkyl,
$R^2$ is alkyl,
$R^4$ represents optionally substituted alkyl,
$R^5$ represents hydrogen or alkyl,
$R^6$ is hydrogen, alkyl or aralkyl, or
the radical of the Formula (VII) constituted by $R^4$, $R^5$ and the carbon and nitrogen atoms attached thereto in the Formula (III)

(VII)

represents a group selected from the groups (A), (B), (C), (D), (E), (F), (G), (H), (I) or (J) of Table 1, which comprises reacting a compound of the general Formula (II) prepared as described above (wherein the meaning of $R^1$ and $R^2$ is as defined above) with a compound of the general Formula (VIII)

wherein $R^4$ is an optionally substituted alkyl, $R^5$ represents hydrogen or alkyl, $R^6$ is hydrogen, alkyl or aralkyl;

or $R^4$ and $R^5$ together represent a group selected from the groups (A), (B), (C), (D), (E), (F), (G), (H), (I), or (J) of Table 1 and $R^6$ is hydrogen or aralkyl or alkyl, or a salt thereof, and if desired, thereafter removing the group $R^6$.

TABLE 1

TABLE 1-continued

According to a still further aspect of the present invention, there is provided a process for the preparation of a compound of the general Formula (III), wherein $R^1$ is phenyl, $R^2$ is ethyl, $R^6$ is hydrogen, and the radical of the Formula (VII) in the general Formula (III) represents a group of the Formula (C) of Table 1 [ramipril], which comprises reacting a compound of the general Formula (II) prepared as described above (wherein the meaning of $R^1$ and $R^2$ is as defined above) with (S,S,S)-2-azabicyclo[3.3.0]octane-carboxylic acid benzylester or its salt, preferably its hydrochloride, and thereafter removing the benzyl group by catalytic hydrogenation.

According to a still further aspect of the present invention there is provided a process for the preparation of ramipril, which comprises reacting the compound of the general Formula (II) prepared according to the above described process wherein $R^1$ represents phenyl and $R^2$ represents ethyl, with (S,S,S)-2-azabicyclo[3.3.0]octane-3-carboxylic acid.

According to another aspect of our invention, there is provided a process for the preparation of a compound of the general Formula (III) (wherein $R^1$ represents methyl, $R^2$ is ethyl, $R^6$ is hydrogen and the meaning of the radical of the Formula (VII) in the general Formula (III) is the group of the Formula (B) in Table 1) [perindopril] and of its salt formed with tertiary butylamine, which comprises reacting the compound of the general Formula (II) prepared according to the above described process wherein $R^1$ is methyl, $R^2$ is ethyl, with (S,S,S)-perhydroindole-2-carboxylic acid benzylester or its salt, preferably its tosylate, thereafter removing the benzyl group by catalytic hydrogenation and subsequently converting the product perindopril thus obtained into its salt formed with tertiary butylamine.

According to a still further aspect of the present invention, there is provided a process for the preparation of perindopril and its tertiary butylammonium salt, which comprises reacting the compound of the general Formula (II) prepared by the above described process (wherein $R^1$ represents methyl and $R^2$ represents ethyl), with (S,S,S)-perhydroindole-2-carboxylic acid and converting the product perindopril into its tertiary butylamine salt.

TECHNICAL BACKGROUND OF THE INVENTION

Figure 1:
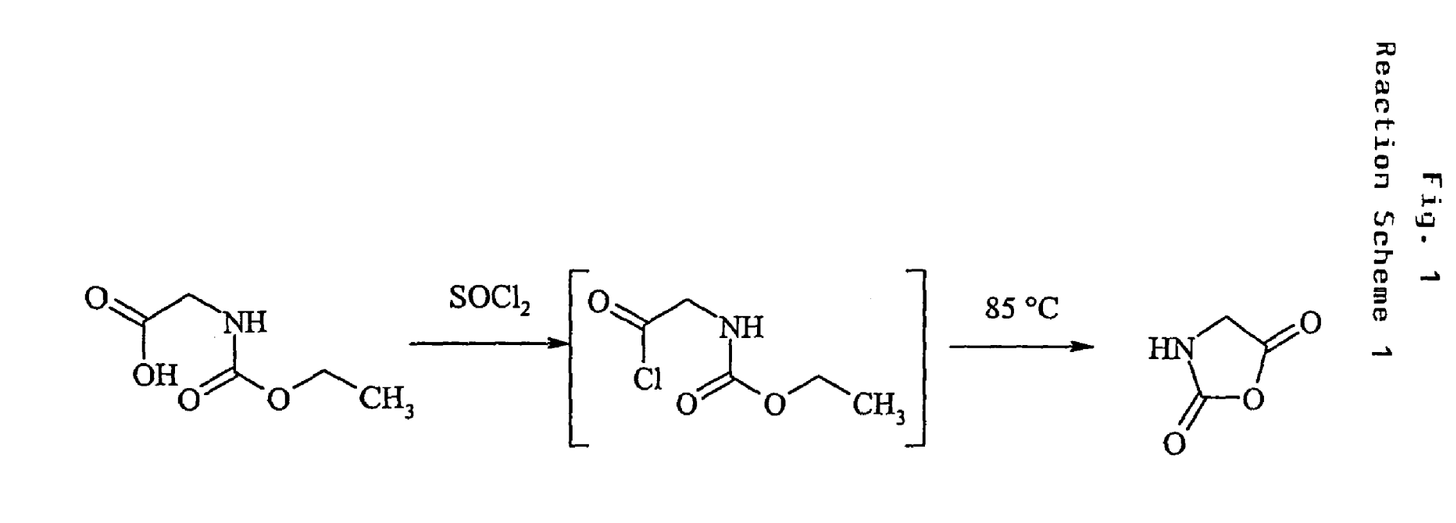
FIG. 1 is a schematic diagram showing Reaction Scheme 1 where N-ethoxycarbonylglycine is reacted with thionyl chloride to form an acyl chloride intermediate which is heated to 85° C. to yield the corresponding cyclic anhydride.

Oxazolidinedione-type compounds were prepared for the first time by reacting N-ethoxycarbonyl-glycine with thionyl chloride and heating the acyl chloride intermediate at 85° C. to yield the corresponding cyclic anhydride (Leuchs, *Chem. Ber.*, 39, 1906, 858). This reaction is demonstrated on FIG. 1 in Reaction Scheme 1.

There are several processes known according to the state of the art for the preparation of the compounds of the general Formula (II). Usually amino acids of the general Formula (IV) are used as starting compounds.

Figure 2:
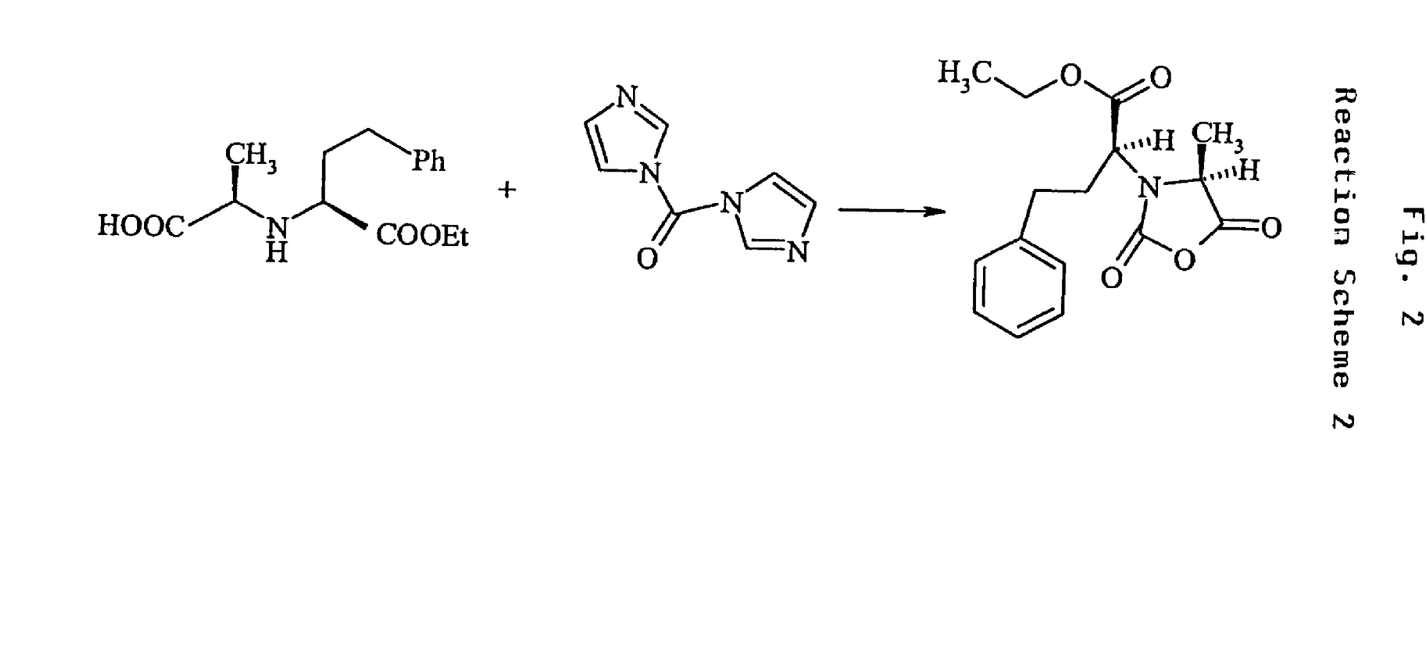
FIG. 2 is a schematic diagram showing Reaction Scheme 2 where a mixture of N-[1-(S)-ethoxycarbonyl-3-phenylpropyl]-L-alanine of the Formula (IV) where $R^1$ is phenyl and $R^2$ is ethyl and N,N'-carbonyl-diimidazole are refluxed in a nitrogen atmosphere for 15 minutes to obtain N-[1-(S)-ethoxycarbonyl-3-phenylpropyl]-4-(S)-methyl-oxazolidine-2,5-dione of the Formula (II).

Oxazolidinediones of the general Formula (II) are prepared by the reaction of the amino acids of the general Formula (IV) and phosgene derivatives. The reaction products were often not isolated, even their formation was not mentioned, but said intermediates were reacted immediately in situ in a peptide coupling reaction. Likewise, in the first process directed to the preparation of N-[1-(S)-ethoxycarbonyl-3-phenylpropyl]-4-(S)-methyl-oxazolidine-2,5-dione (compound of general Formula (II) wherein $R^1$ is phenyl, $R^2$ is ethyl), the mixture of N-[1-(S)-ethoxycarbonyl-3-phenylpropyl]-L-alanine (compound of Formula (IV), wherein $R^1$ is phenyl, $R^2$ is ethyl) and N,N'-carbonyl-diimidazole was refluxed in nitrogen atmosphere for 15 minutes and the solution thus obtained was directly used in subsequent reaction steps (Jerry W. Skiles, Raymond D. Youssefyeh, John T Suh, Howard Jones EP 61768, 29 Mar. 1982). This process is demonstrated on FIG. 2 in Reaction Scheme 2.

Oxazolidinediones of the general Formula (II) were prepared, isolated and characterized by other authors in a similar way by using N,N'-carbonyl-diimidazole (Oudenes, Jan y Schleicher, Richard Henry ES 2004804, 1 Feb. 1989; Marjo Mrslavic, Janja Crinski U.S. Pat. No. 5,359,086, 16 Sep. 1993).

According to a frequently used process also known according to the state of the art, oxazolidinediones of the general Formula (II) are prepared by reacting the amino acid of the general Formula (IV) and phosgene (Fu-chih Huang, Howard Jones, Clara J. Lin, Bernard Loev EP 114067, 12 Jan. 1983; Raymond D. Youssefyeh, Jerry W. Skiles, John T. Suh, Howard Jones, U.S. Pat. No. 4,686,295, 7 Mar. 1983; Satomi Takahashi, Kenji Inoue, Yoshyfumi Yanagida, Takehisa Ohashi, Kiyoshi Watanabe EP 215335, 23 Aug. 1986).

Another known process utilizes trichloromethyl chloroformate as a further phosgene derivative for the preparation of oxazolidinediones of the general Formula (II) (Satomi Takahashi, Kenji Inoue, Takehisa Ohashi, Kiyoshi Watanabe U.S. Pat. No. 4,716,235, 29 Dec. 1987).

According to a still further known process, the less toxic triphosgene has been used instead of phosgene (Pau Cid EP 1279665 23 Jul. 2002)

According to a further known process, the compounds of the general Formula (IV) were transformed into compounds of their N-alkoxy(aralkoxy)-carbonyl derivatives of the general Formula (V)

and said derivatives were used for the preparation of the compounds of general Formula (II).

Figure 3:
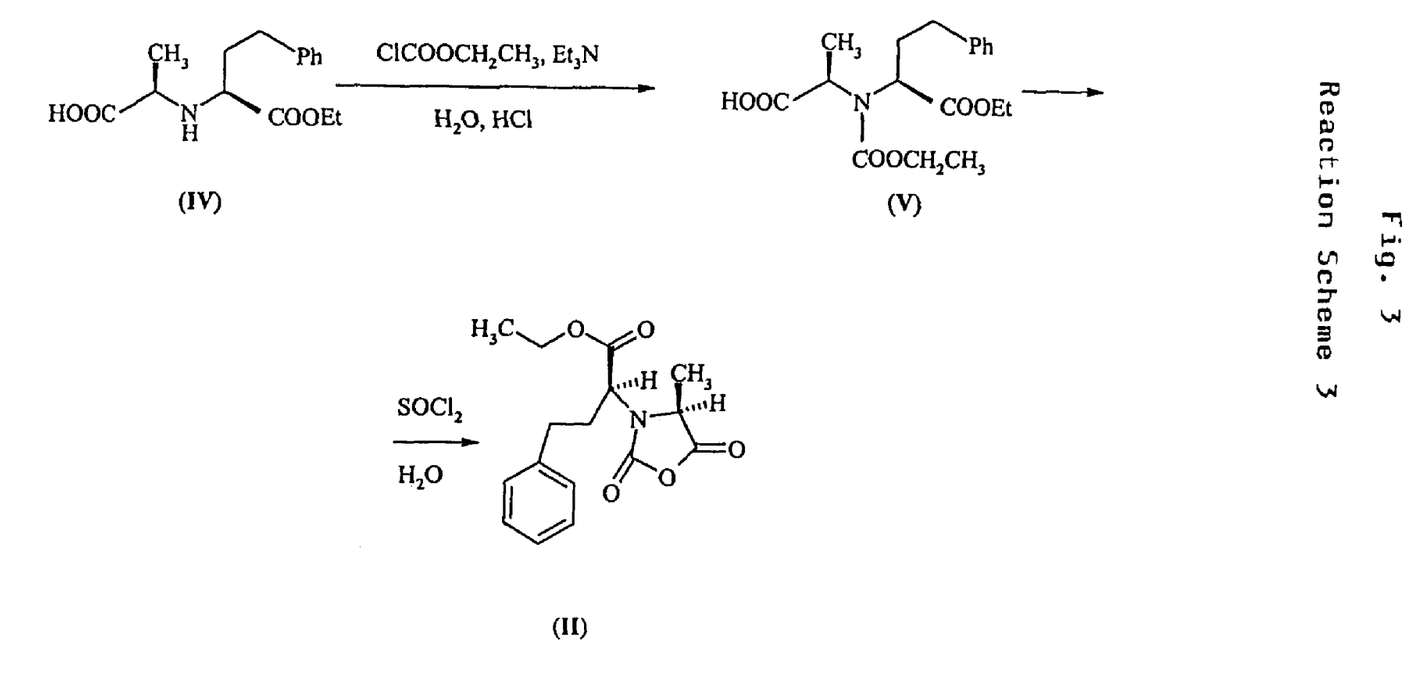
FIG. 3 is a schematic diagram showing Reaction Scheme 3 where an amino acid of the Formula (IV) where $R^1$ is phenyl and $R^2$ is ethyl, is reacted with ethyl chloroformate in dichloroethane to obtain a compound of the Formula (V) where $R^1$ is phenyl and $R^2$ and $R^3$ are each ethyl, which is then reacted with a carbonyl group activating agent, such as thionyl chloride, acetyl chloride, or acetic anhydride to yield the corresponding oxazolidinedione of the Formula (II).

European Patent No. 1 197 490 (inventors: Chong-Ming Chen, Yu-Liang Liu, Ya-Chieh Chai, Chien-Huang Wu. application date, 15 May 2001.) discloses the reaction between the amino acids of general Formula (IV) (wherein $R^1$ represents phenyl and $R^2$ represents ethyl) and 1.2 molar equivalents of ethyl chloroformate in dichloroethane, whereupon the compound of general Formula (V) thus formed (wherein $R^1$ is phenyl and $R^2$ and $R^3$ each represents ethyl) was reacted with a carboxyl group activating reagent, e.g. thionyl chloride, acetyl chloride or acetic anhydride to yield the corresponding oxazolidinedione of general Formula (II). This process is demonstrated on FIG. 3 in Reaction Scheme 3.

SUMMARY OF THE INVENTION

Figure 4:
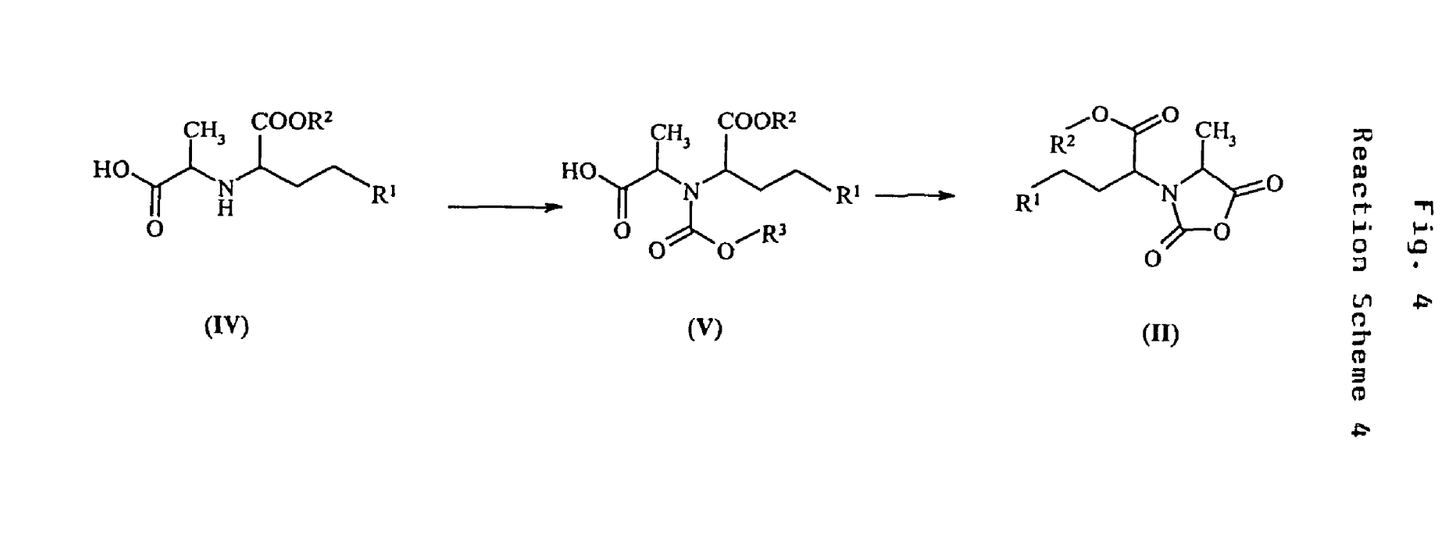
FIG. 4 is a schematic diagram showing Reaction Scheme 4 where a compound of the Formula (IV) is reacted with a compound of the Formula (VI) to form an intermediate compound of the Formula (V) which is then converted to a compound of the Formula (II).

In the course of our research we intended to prepare cyclic anhydrides of the general Formula (II). The Reaction Scheme 4 is illustrated on FIG. 4 starting from the compounds of the general Formula (IV) via the intermediates of the general Formula (V).

When carrying out the process of European Patent No. 1 197 490 and monitoring the reaction by chromatography, it has been found that when using the compound of the general Formula (VI) in slight molar excess only, the starting material of the general Formula (IV) is consumed extremely slowly, the desired product corresponding to the general Formula (V) is formed similarly slowly and according to the chromatographic analysis, there is a by-product present besides the desired product of the general Formula (V), after the starting compound is used up in the reaction.

The present invention is based on the surprising recognition that when using the compound of the general Formula (VI) in at least 2 molar equivalents related to the amount of the compound of the general Formula (IV), the reaction proceeds rapidly and results in a homogeneous product, which has been isolated and identified as a compound of the general Formula (I), wherein $R^1$ represents alkyl or aryl, $R^2$ represents alkyl and $R^3$ represents alkyl or aralkyl. The compounds of the general Formula (I) are new.

DETAILED DESCRIPTION OF THE INVENTION

Mixed anhydrides of amino acids similar to the compounds of the general Formula (I) are known from prior art. Said compounds are usually prepared starting from N-alkoxy (aralkoxy)-carbonyl amino acids (for a general process of preparation, see: Org Synth. Vol. 63, 160-168, Ed Wiley 1985) in an organic solvent (usually N,N-dimethylformamide or tetrahydrofurane) and in the presence of N-methylmorpholine by adding a 1 molar equivalent amount of the alkyl or aralkyl chloroformate of the general Formula (VI) at −20° C. Such mixed anhydrides may contain two identical alkoxy (aralkoxy)-carbonyl groups, but, in the majority of the cases, the two groups are different. According to the teaching of prior art, the object of the preparation of such a mixed anhydride is to increase the reactivity of the carboxyl groups in the subsequent reaction, which can be a coupling reaction to yield peptides (D. Jukic et al., Eur. J. Med. Chem. 1991, 921), chain extension (J. Cooper et al., J. Chem. Soc. Perkin Trans. 1, 1991, 705), synthesis of acyl derivatives, such as a thioester or an amide (R. A. Breitenmoser et al., Helvetica. Chim. Acta 2001, 786; B. Garrigues et al., Tetr. Lett. 1986, 1685) and the reduction of the carboxy group to a hydroxymethyl group to yield alcohols (V. Constantinou-Kokotou, Org. Prep. Proced. Int. 1999, 237; V. Caplar et al., Croatica Chim. Acta 2003, 23).

Prior art is silent in teaching a process for the conversion of compounds similar to those of the general Formula (I) into oxazolidinediones.

The further surprising recognition serving as a basis of the present invention is that oxazolidinediones of the general Formula (II) are formed in the reaction of the compound of the general Formula (I) and thionyl chloride. Said process provides an outstanding possibility for the synthesis of the compounds of the general Formula (II) on an industrial scale. Namely, the novel intermediates of the general Formula (I) are produced in a rapid reaction and are obtained in the form of highly pure and homogeneous product which can be isolated in extremely high purity. The conversion of the compounds of the general Formula (I) into the corresponding oxazolidinediones of the general Formula (II) can be easily and simply performed on an industrial scale.

The oxazolidinediones of the general Formula (II) are important intermediates, useful in the preparation of the compounds of the general Formula (III).

In the general Formula (III),
$R^1$ represents aryl or alkyl;
$R^2$ represents alkyl,
$R^4$ represents optionally substituted alkyl,
$R^5$ represents hydrogen or alkyl, or
the radical of the Formula (VII) constituted by $R^4$, $R^5$ and the carbon and nitrogen atoms attached thereto in the general Formula (III) is part of a ring system of the Formula (A), (B), (C), (D), (E), (F), (G), (H), (I) or (J) of Table 1; and
$R^6$ is hydrogen, alkyl or aralkyl.

Among the compounds of the general Formula (III) there are several important antihypertensive pharmaceutically active agents, such as ramipril, perindopril and enalapril.

The definitions for the terms used in the present specification are the following:

The term "alkyl" represents a straight or branched, saturated, aliphatic hydrocarbon group comprising 1 to 6, preferably 1 to 4 carbon atoms, e.g. methyl, ethyl, 1-propyl, 2-propyl, 1-butyl, tertiary butyl etc.

Under the term "aryl" are meant aromatic hydrocarbon groups comprising one or more aromatic rings, which can be substituted by one or more identical or different substituents, e.g. halogen, alkyl, alkoxy, hydroxy, amino, etc.

The meaning of the term "aralkyl" is alkyl substituted by one or more aryl groups, e.g. benzyl, phenylethyl, β,β'-diphenylethyl, etc.

A preferable representative of the compounds of the general Formula (I) is the compound wherein $R^1$ represents phenyl, $R^2$ and $R^3$ each represents ethyl, which is a valuable intermediate useful in the synthesis of the antihypertensive drug known by the International Nonproprietary Name (INN) ramipril.

A second preferred representative of the compounds of the general Formula (I) is the compound wherein $R^1$ represents methyl, $R^2$ and $R^3$ each represents ethyl, which is a valuable intermediate useful in the synthesis of the antihypertensive drug known by the International Nonproprietary Name (INN) perindopril.

The compounds of the general Formula (I) can be prepared by reacting a compound of the general Formula (IV) in an organic solvent with at least 2 molar equivalents of a compound of the general Formula (VI) in the presence of an acid-binding reagent. In the reaction the compound of the general Formula (VI) is advantageously used in a 2 to 3 molar equivalent amount, preferably in a 2.2 molar equivalent amount related to the starting compound of the general Formula (IV).

As organic solvent, preferably tetrahydrofurane, ethyl acetate, dichloromethane or acetone, especially advantageously acetone can be used.

As acid-binding reagent, organic amines (e.g. triethylamine, pyridine, morpholine) or inorganic salts (e.g. sodium carbonate, potassium carbonate) can be used. Especially advantageously, triethylamine can be used.

In the starting compounds of the general Formula (VI), X preferably stands for chlorine. In the compounds of the general Formula (VI), $R^3$ preferably represents ethyl.

The reaction takes place easily at about room temperature. The reaction time is short, usually about 1 hour.

According to the present invention, a compound of the general Formula (I) can be converted into the corresponding compound of the general Formula (II) by treatment with thionyl chloride in an organic solvent.

Thionyl chloride can be used in equimolar amount with the compound of the general Formula (I) or said reagent can be used in a 1.5-2.5 molar excess related to the molar amount of the reactant of the general Formula (I).

According to a preferable embodiment of the process, the compound of the general Formula (I) can be used wherein $R^1$ represents phenyl and $R^2$ and $R^3$ both represent ethyl. In this case, a compound of the general Formula (II) useful in the synthesis of ramipril is obtained.

In a further preferable embodiment of the process, the compound of the general Formula (I) wherein $R^1$ represents methyl and $R^2$ and $R^3$ each represent ethyl can be used. In this case, a compound of the general Formula (II) useful in the synthesis of perindopril is obtained.

In the process, organic solvents selected from the group of aprotic solvents, preferably dichloromethane, can be used.

The reaction proceeds easily even at low temperature. Said reaction can be carried out between about 5° C. and about room temperature. The reaction time is several hours.

The advantage of the above mentioned process resides in the fact that the intermediates of the general Formula (I) are obtained in the form of homogeneous, high-purity products and the conversion of said compounds of the general Formula (I) into the compounds of the general Formula (II) can be accomplished in an easily feasible way on the industrial scale by a simple process.

The compounds of the general Formula (II) prepared according to the above described process can be converted into the end products of the general Formula (III) by methods known from prior art.

According to a further aspect of the present invention, there is provided a method for the preparation of the compounds of the general Formula (III), wherein $R^1$ is aryl or alkyl;
$R^2$ represents alkyl;
$R^4$ represents an optionally substituted alkyl;
$R^5$ represents hydrogen or alkyl, or
the radical of the Formula (VII) constituted by $R^4$, $R^5$ and the carbon and nitrogen atoms attached thereto in the general Formula (III) is part of a ring system selected from (A), (B), (C), (D), (E), (F), (G), (H), (I) or (J) of Table 1, and
$R^6$ represents hydrogen, alkyl or aralkyl,
which comprises reacting a compound of the general Formula (II) prepared according to the above process (wherein the meaning of $R^1$ and $R^2$ is defined above) with a compound of the general Formula (VIII) or its salt (wherein $R^4$, $R^5$ and $R^6$ are as defined above), and if desired, converting the ester of the general Formula (III) thus obtained (wherein the meaning of $R^6$ is alkyl or aralkyl) into a carboxylic acid of the general Formula (III) (wherein the meaning of $R^6$ is hydrogen); and, if desired, transforming the compound of the general Formula (III) obtained in the above process into its salt.

Compounds of the general Formula (VIII) can be used as their salts, such as hydrogen halogenides (e.g. hydrochloride) or as alkyl- or aryl sulfonates (e.g. tosylate).

The reaction of the compounds of the general Formulae (II) and (VIII) can be performed according to methods known from the prior art.

The conversion of the esters, wherein $R^6$ represents alkyl or aralkyl, into the corresponding carboxylic acids, wherein the meaning of $R^6$ is hydrogen, as well as the salt formation of said carboxylic acids can be performed according to the methods known from the prior art.

The above described aspect of the present invention can be especially preferably utilized for the preparation of the compounds of the general Formula (III), wherein $R^1$ is phenyl, $R^2$ is ethyl, $R^6$ is hydrogen and the radical of the Formula (VII) is part of the ring system (A) (enalapril), (B) (trandolapril), (C) (ramipril) or (E) (quinapril) in Table 1.

A similar preferable utilization of the above process is its use for the preparation of the compounds of the general Formula (III), wherein $R^1$ is methyl, $R^2$ is ethyl, $R^6$ is hydrogen and the radical of the Formula (VII) is part of the ring system (B) in Table 1 (perindopril).

According to a further aspect of the present invention there is provided a process for the preparation of ramipril, which comprises reacting the compound of the general Formula (II) prepared as described above (wherein $R^1$ represents phenyl and $R^2$ represents ethyl) with (S,S,S)-2-azabicyclo[3.3.0]octane-3-carboxylic acid benzylester or its salt, preferably its hydrochloride, and subsequently removing the benzyl group by catalytic hydrogenation.

According to a still further aspect of the present invention there is provided a process for the preparation of perindopril, which comprises reacting the compound of the general Formula (II) prepared as described above (wherein $R^1$ represents methyl and $R^2$ represents ethyl) with (S,S,S)-perhydroindole-2-carboxylic acid benzylester or its salt, preferably its hydrochloride, and subsequently removing the benzyl group by catalytic hydrogenation.

The reaction is carried out in a manner known in the art, using an organic solvent and an acid-binding reagent. As organic solvent, ethyl acetate can be advantageously used.

Suitable acid-binding reagents include organic bases, e.g. triethylamine or inorganic salts, e.g. sodium carbonate or potassium carbonate.

The reaction can be performed at about 5° to about 10° C. The reaction time is usually several hours.

The benzyl group can be removed from the product by catalytic hydrogenation. Suitable catalysts include noble metals. Preferably palladium or platinum, especially preferably, palladium can be used.

As a reaction medium, polar organic solvents, preferably ethanol can be used.

According to the present invention, an alternative method is provided for the preparation of ramipril, which comprises reacting the compound of the general Formula (II), wherein $R^1$ is phenyl and $R^2$ is ethyl, with (S,S,S)-2-azabicyclo [3.3.0]-octane-3-carboxylic acid.

Similarly, perindopril can be prepared by reacting the compound of the general Formula (II), wherein $R^1$ is methyl and $R^2$ is ethyl, with (S,S,S)-perhydroindole-2-carboxylic acid.

The coupling reaction can be preferably performed using tetrahydrofurane as solvent by refluxing the reaction mixture for several hours.

The advantage of the above mentioned process resides in the fact that the intermediate compounds of the general Formula (I) are obtained as homogeneous products of high purity, and conversion of said compounds of the general Formula (I) into the compounds of the general Formula (II) can be accomplished in an easily feasible way on the industrial scale in a simple process.

Further details of the present invention are to be found in the following Examples without limiting the scope of the invention to said Examples.

EXAMPLE 1

Ethyl 2-(S)-{N-ethoxycarbonyl-N-[1-(S)-(ethoxycarbonyloxycarbonyl)-ethyl]-amino}-4-phenylbutyrate 2.79 g (0.01 mole) of N-[1-(S)-ethoxycarbonyl-3-phenyl-propyl]-L-alanine is suspended in 25 ml acetone whereupon 2.02 g (2.8 ml; 0.02 mole) of triethylamine are added. The reaction mixture is stirred until all starting materials are completely dissolved. 2.39 g (2.1 ml, 0.022 mole) of ethyl chloroformate is added dropwise to the reaction mixture while keeping the temperature between 10 and 20° C. Subsequently the reaction mixture is stirred at room temperature for one hour. After stirring, the reaction mixture is cooled and stirred at a temperature between −2 and 2° C. for 30 minutes. The crystalline precipitate is filtered off and the filtrate is concentrated by evaporation. The product is obtained as a viscous oil (yield 4.20 g, approx. 100%).

IR (cm$^{-1}$) 3063, 1827, 1742, 1710.

$^1$H-NMR (CDCl$_3$) δ 7.25 (5H, m, ArH$_{2-6}$); 4.55 (1H, t, PhCH$_2$CH$_2$CH), 4.34 (2H, q, J=7.0 Hz, OCH$_2$CH$_3$), 4.30-4.05 (5H, m, Ala α-H, 2×OCH$_2$CH$_3$); 2.85-2.75 (2H, m, PhCH$_2$); 2.35-2.20 (1H, m, PhCH$_2$CH$_2$); 2.20-1.95 (1H, m, PhCH$_2$CH$_2$); 1.55 (3H, d, J=7.0 Hz, Ala-CH$_3$); 1.35 (3H, t, J=7.0 Hz, OCH$_2$CH$_3$); 1.27 (6H, t, J=7.3 Hz, 2×CH$_3$) ppm.

Elemental analysis C$_{21}$H$_{29}$NO$_8$ (423.47)

Calculated C, 59.56; H, 6.90; N, 3.31%

Measured C, 59.16; H, 6.81; N, 3.41%

EXAMPLE 2

N-[1-(S)-Ethoxycarbonyl-3-phenylpropyl]-4-(S)-methyl-oxazolidine-2,5-dione a) 4.23 g (0.01 mole) of ethyl 2(S)-{N-ethoxycarbonyl-N-[1 (S)-(ethoxycarbonyloxy-carbonyl)-ethyl]-amino}-4-phenylbutyrate is dissolved in 10 ml of dichloromethane and to this solution is added dropwise 1.93 g (1.18 ml, 0.0165 mole) of thionyl chloride while keeping the temperature of the reaction mixture between 5 and 10° C. Subsequently the reaction mixture is stirred at room temperature for 4.5-5 hours. The solvent is evaporated from the reaction mixture. The resulting brown, viscous oil is dissolved in 3.5 ml of methyl-tertiary butyl ether, stirred at a temperature between −10 and −5° C. and the precipitated crystals are isolated by filtration. Yield 1.95 g (64%), colorless crystals. Melting point 67-68° C.

b) 2.79 g (0.01 mole) N-[1-(S)-Ethoxycarbonyl-3-phenylpropyl]-L-alanine is suspended in 25 ml acetone and 2.02 g (2.8 ml; 0.02 mole) of triethylamine is added to the suspension. The reaction mixture is stirred until all solids are dissolved and 2.17 g (1.9 ml, 0.02 mole) of ethyl chloroformate is added dropwise, while maintaining the temperature of the reaction mixture between 10 and 20° C. The reaction mixture is stirred at room temperature for 1 hour. Subsequently the reaction mixture is cooled and stirred for 30 minutes at a temperature between −2 and 2° C. The crystalline precipitate is filtered off and the filtrate is evaporated to dryness.

The oily residue is dissolved in 10 ml dichloromethane, cooled to 5° C. and 1.93 g (1.18 ml, 0.0165 mol) of thionyl chloride is added dropwise while keeping the temperature of the reaction mixture between 5 and 10° C.

Subsequently the reaction mixture is stirred at room temperature for 4.5 to 5 hours. The solvent is evaporated and the resulting brown, viscous oil is mixed with 3.5 ml methyl-tertiary butyl ether. The solution is stirred at a temperature between −10 to −5° C. and the crystalline product is isolated by filtration.

Yield 1.95 g, (64%), colorless crystals.
Melting point, 67-68° C.
IR (cm$^{-1}$) 2980, 2930, 1845, 1770, 1725.
$^1$H-NMR (CDCl$_3$) δ 7.25 (5H, m, ArH$_{2-6}$); 4.40 (1H, q, J=7.0 Hz, Ala α-H); 4.36 (1H, dd, J=5.0 Hz, PhCH$_2$CH$_2$CH), 4.23 (2H, q, J=7.1 Hz, OCH$_2$CH$_3$); 2.80 (2H, m, PhCH$_2$); 2.50-2.40 (1H, m, PhCH$_2$CH$_2$); 2.35-2.25 (1H, m, PhCH$_2$CH$_2$); 1.54 (3H, d, J=7.0 Hz, Ala-CH$_3$); 1.28 (3H, t, J=7.1 Hz, OCH$_2$CH$_3$) ppm.
Elemental Analysis C$_{16}$H$_{19}$NO$_5$ (305.33)
Calculated C, 62.94; H, 6.27; N, 4.59%
Measured C, 62.90; H, 6.15; N, 4.67%

EXAMPLE 3

(2S,3aS,6aS)-1-[(2S)-2-[[(1S)-1-(Ethoxycarbonyl)-3-phenylpropyl]amino]-1-oxopropyl]-octahydrocyclopenta[b]pirrole-2-carboxylic acid (Ramipril)

25.0 g (0.0887 mole) of (S,S,S)-2-Azabicyclo[3.3.0]octane-3-carboxylic acid benzylester hydrochloride and 9.9 g (13.5 ml; 0.0975 mol) of triethylamine are mixed with 125 ml ethyl acetate. To the resulting suspension, solution of 32.5 g (0.1065 mole) of N-[1-(S)-ethoxycarbonyl-3-phenylpropyl]-4-(S)-methyl-oxazolidine-2,5-dione in 125 ml ethyl acetate is added dropwise while keeping the reaction temperature between 5-10° C. Subsequently, the reaction mixture is stirred at room temperature for four hours.

After the stirring period, the reaction mixture is cooled to a temperature between 0 and 5° C. and the salt is filtered off. The filtrate is washed with water (2×200 ml), dried over magnesium sulfate and the solvent is evaporated to dryness. The obtained crude ramipril benzylester is hydrogenated in 96 (v/v) % ethanol (440 ml) using palladium/charcoal catalyst. The reaction mixture is evaporated to dryness, the evaporation residue is stirred in diisopropyl ether (260 ml) at 0-5° C. for one hour and the product is filtered off. Thus 32.2 g (87%) crude product is obtained.

The product is recrystallized from the mixture of diethyl-ether/diisopropylether yielding 27.3 g (74%) purified product.

Melting point, 107-108° C.
The IR and $^1$H-NMR spectra of the product are identical with that of the United States Pharmacopoeial Certified Reference Standard.
Elemental Analysis C$_{23}$H$_{32}$N$_2$O$_5$ (416.53)
Calculated: C, 66.32; H, 7.74; N, 6.73%
Measured: C, 66.37; H, 7.75; N, 6.64%

EXAMPLE 4

Ethyl 2-(S)-{N-ethoxycarbonyl-N-[1-(S)-(ethoxycarbonyloxycarbonyl)-ethyl]amino}-pentanoate 2.17 g (0.01 mole) of N-[1-(S)-ethoxycarbonyl-butyl]-L-alanine is suspended in 25 ml acetone and 2.02 g (2.8 ml; 0.02 mole) of triethylamine is added. The reaction mixture is stirred until all solids are dissolved and 2.39 g (2.1 ml, 0.022 mole) of ethyl chloroformate is added dropwise while keeping the temperature of the reaction mixture between −5 and 0° C. The reaction mixture is stirred at room temperature for 1 hour. After this period, the reaction mixture is cooled and stirred for 30 minutes at a temperature between −2 and 2° C. The crystalline solid is filtered off and the filtrate is evaporated to dryness in vacuo. The product is obtained as a viscous oil (3.40 g, 94%).

IR (cm$^{-1}$) 2981, 1827, 1742, 1712
$^1$H-NMR (CDCl$_3$) δ 4.70 (1H, t, CH$_3$CH$_2$CH$_2$CH), 4.31 (2H, q, J=7.0 Hz, OCH$_2$CH$_3$), 4.30 (1H, q, J=7.0 Hz, Ala α-H) 4.24-4.10 (4H, m, 2×OCH$_2$CH$_3$); 1.98-1.70 (1H, m, CH$_3$CH$_2$CH$_2$); 1.70-1.60 (1H, m, CH$_3$CH$_2$CH$_2$); 1.55 (3H, d, J=7.0 Hz, Ala-CH$_3$); 1.47-1.33 (2H, m, CH$_3$CH$_2$CH$_2$); 1.37 (3H, t, J=7.0 Hz, OCH$_2$CH$_3$); 1.27 (3H, t, J=7.3 Hz, OCH$_2$CH$_3$); 1.26 (3H, t, J=7.3 Hz, OCH$_2$CH$_3$); 0.97 (3H, t, J=7.3 Hz, CH$_3$CH$_2$CH$_2$) ppm.
Elemental Analysis C$_{16}$H$_{27}$NO$_8$ (361.40)
Calculated C, 53.18; H, 7.53; N, 3.88%
Measured: C, 52.90; H, 7.47; N, 4.03%

EXAMPLE 5

N-[1-(S)-Ethoxycarbonyl-butyl]-4-(S)-methyl-oxazolidine-2,5-dione a) 3.61 g (0.01 mole) of ethyl 2(S)-{N-ethoxycarbonyl-N-[1 (S)-(ethoxycarbonyloxy-carbonyl)-ethyl]-amino}-pentanoate is dissolved in 10 ml dichloromethane and 1.93 g (1.18 ml; 0.0165 mole) of thionyl chloride is added dropwise, while keeping the temperature of the reaction mixture between 5 and 10° C. Subsequently the reaction mixture is stirred at room temperature for 2 to 3 hours. After the stirring period, the solvent is evaporated from the reaction mixture. The product is obtained in oily form as the distillation residue (yield 2.31 g, 95%).

b) 2.17 g (0.01 mole) N-[1-(S)-Ethoxycarbonyl-butyl]-L-alanine is suspended in 25 ml acetone and to this suspension is 2.02 g (2.8 ml; 0.02 mole) of triethylamine added. The suspension is stirred until all solids are dissolved and 2.17 g (1.9 ml, 0.02 mole) of ethyl chloroformate is added dropwise to the reaction mixture while maintaining the reaction temperature between 10 and 20° C. The reaction mixture is subsequently stirred at room temperature for one hour, cooled and stirred for 30 minutes at a temperature between −2 and 2° C. The crystalline solid is filtered off and the filtrate is evaporated to dryness.

The resulting oily residue is dissolved in 10 ml of dichloromethane, cooled to 5° C. and while the temperature of the reaction mixture is kept between 5 and 10° C., 1.93 g (1.18 ml; 0.0165 mol) of thionyl chloride is added dropwise. Subsequently the reaction mixture is stirred at room temperature for 2 to 3 hours. After the stirring period, the solvent is evaporated from the reaction mixture. The product is obtained as oil (yield 2.31 g, 95%).

IR (cm$^{-1}$): 2980, 2966, 1852, 1780, 1739

$^1$H-NMR (CDCl$_3$) δ 4.59 (1H, q, J=7.0 Hz, Ala α-H); 4.48 (1H, dd, J=5.7 Hz, CH$_3$CH$_2$CH$_2$CH); 4.23 (2H, q, J=7.1 Hz, OCH$_2$CH$_3$); 2.07-1.98 (1H, m, CH$_3$CH$_2$CH$_2$CH); 1.94-1.84 (1H, m, CH$_3$CH$_2$CH$_2$CH); 1.59 (3H, d, J=7.0 Hz, Ala-CH$_3$); 1.56-1.41 (2H, m, CH$_3$CH$_2$CH$_2$CH); 1.30 (3H, t, J=7.1 Hz, OCH$_2$CH$_3$); 0.99 (3H, t, J=7.4 Hz, CH$_3$CH$_2$CH$_2$CH) ppm.

Elemental Analysis C$_{11}$H$_{17}$NO$_5$ (243,265)
Calculated: C, 54.31; H, 7.04; N, 5.76%
Measured: C, 53.74; H, 7.15; N, 5.70%

EXAMPLE 3

(2S,3aS,7aS)-1-[(2S)-2-[[(1S)-1-(Ethoxycarbonyl)butyl]amino]-1-oxopropyl]octahydro-1H-indole-2-carboxylic acid tertiary butylammonium salt (Perindopril erbumin)

a) 4.72 g (28 mmole) of (S,S,S)-1H-Perhydroindole-2-carboxylic acid is suspended in 37.5 ml of tetrahydrofurane and the suspension is cooled to 0-5° C. To the suspension, a solution of 8.15 g (33.5 mmole) N-[1-(S)-ethoxycarbonyl-butyl]-4-(S)-methyl-oxazolidine-2,5-dione in 37.5 ml tetrahydrofurane is added dropwise while maintaining the reaction temperature between 0 and 5° C. Subsequently the reaction mixture is stirred and refluxed for four hours.

The reaction mixture is evaporated in vacuo and the evaporation residue is dissolved in 120 ml ethyl acetate. Solution of 1.95 g (2.8 ml, 27 mmole) of tertiary butylamine in 60 ml ethyl acetate is added dropwise to the ethylacetate solution of the evaporation residue under stirring. The resulting suspension is heated until dissolved, treated with activated carbon, filtered and the filtrate is allowed to cool to room temperature with continuous stirring. The crystalline product is filtered off. Yield, 6.76 g (55%).

Melting point, 149.0-149.5° C.

The IR and $^1$H-NMR spectra of the product are identical to those of the originator.

b) To a solution of 12.95 g (0.03 mole) of (S,S,S)-1H-perhydroindole-2-carboxylic acid benzylester tosylate and 9.10 g (12.5 ml, 0.09 mole) of triethylamine in 90 ml ethyl acetate, a solution of 8.76 g (0.036 mole) N-[1-(S)-ethoxycarbonyl-butyl]-4-(S)-methyl-oxazolidine-2,5-dione in 90 ml ethyl acetate is added dropwise at room temperature. The reaction mixture is stirred at room temperature for 2 hours. After the stirring period, the reaction mixture is mixed with 150 ml of 5 (w/v) % aqueous solution of sodium hydrogencarbonate, the organic layer is separated, washed with water (2×150 ml), dried over magnesium sulfate, treated with activated carbon, filtered and evaporated to dryness.

The thus obtained crude perindopril benzylester is dissolved in 150 ml of ethanol and hydrogenated in the presence of palladium/charcoal catalyst. The catalyst is filtered off, the solvent is evaporated and the evaporation residue is dissolved in 120 ml ethyl acetate. To the resulting solution, a solution of 2.19 g (3.15 ml, 0.03 mol) tertiary butylamine in 45 ml of ethyl acetate is added dropwise while stirring. The crystals are filtered off and purified by recrystallization from ethyl acetate. Thus 9.65 g (73%) crystalline product is obtained.

Melting point, 149.0-149.5° C.

The IR and $^1$H-NMR spectra of the product are identical to those of the originator.

The invention claimed is:

1. A compound of the formula (I), wherein

R$^1$ is aryl or alkyl;
R$^2$ is alkyl; and
R$^3$ is alkyl or aralkyl.

2. The compound of the formula (I) according to claim 1, wherein R$^1$ is phenyl, R$^2$ is ethyl and R$^3$ is ethyl.

3. The compound of the formula (I) according to claim 1, wherein R$^1$ is methyl, R$^2$ is ethyl and R$^3$ is ethyl.

4. A process for the preparation of a compound of the formula (I) according to claim 1, wherein the definitions of R$^1$, R$^2$ and R$^3$ are as given in claim 1, comprising the step of:
reacting a compound of the general formula (IV)

in an organic solvent in the presence of an acid-binding reagent with at least 2 molar equivalents of a compound of the formula (VI)

XCOOR$^3$     (VI)

where X is halogen or a tertiary butyloxycarbonyloxy group and the meaning of R$^3$ is as defined above).

5. The process according to claim 4, wherein
one molar equivalent of a compound of the formula (IV) reacts with 2 to 3 molar equivalents of the compound of the formula (VI).

6. The process according to claim 4, wherein
tetrahydrofurane, ethyl acetate, dichloromethane or acetone is employed as the organic solvent.

7. The process according to claim 6, wherein
acetone is employed as the organic solvent.

8. The process according to claim 4, wherein
an organic amine or an inorganic salt is employed as the acid-binding reagent.

9. The process according to claim 8, wherein an acid binding agent is employed, using as the organic amine, triethylamine, pyridine or morpholine; and as the inorganic salt, sodium carbonate or potassium carbonate.

10. The process according to claim 9, wherein triethylamine is employed as the acid-binding reagent.

11. The process according to claim 4, wherein a compound of the formula (VI) is employed wherein X is chlorine and $R^3$ is ethyl.

12. A process for the preparation of a compound of the formula (II)

wherein
$R^1$ is aryl or alkyl; and
$R^2$ is alkyl
comprising the step of:
reacting a compound of the formula (I)

wherein
$R^1$ is aryl or alkyl;
$R^2$ is alkyl; and
$R^3$ is alkyl or aralkyl,
with thionyl chloride in an organic solvent.

13. The process according to claim 12, in which the compound of the formula (I) is employed wherein $R^1$ is phenyl, $R^2$ is ethyl, and $R^3$ is ethyl.

14. The process according to claim 12, in which the compound of the formula (I) is employed wherein $R^1$ is methyl, $R^2$ is ethyl, and $R^3$ is ethyl.

15. The process according to claim 12 in which an aprotic solvent is employed as the organic solvent.

16. The process according to claim 15, in which dichloromethane is employed as the aprotic solvent.

17. The process for the preparation of a compound of the formula (II) as defined as in claim 12, in which a compound of the formula (IV)

wherein $R^1$ and $R^2$ are defined as above is reacted in an organic solvent in the presence of an acid-binding reagent with at least 2 molar equivalents of a compound of the formula (VI)

XCOOR³ wherein
X is chloro and
$R^3$ is ethyl, to obtain a compound of the Formula (I)

and thereafter, reacting the compound of the formula (I) thus obtained with thionyl chloride in an organic solvent to obtain the compound of the Formula (II).

18. The process according to claim 17, in which as a starting material, a compound of the formula (IV) is employed wherein $R^1$ is phenyl, and $R^2$ is ethyl and a compound of the formula (VI) is employed wherein $R^3$ is ethyl and X is chlorine.

19. The process according to claim 17, in which as a starting material, a compound of the formula (IV) is employed wherein $R^1$ is methyl, $R^2$ is ethyl and a compound of the formula (VI) is employed wherein $R^3$ is ethyl and X is chlorine.

20. The process according to claim 17, in which one molar equivalent of a compound of the formula (IV) reacts with 2 to 3 molar equivalents of a compound of the formula (VI).

21. The process according to claim 17, in which an organic amine or an inorganic salt is employed as acid-binding reagent.

22. The process according to claim 17, in which triethyl amine, pyridine or morpholine is the organic amine employed as the acid binding reagent.

23. The process according to claim 22, in which triethyl amine is the organic amine employed as the acid-binding reagent.

24. The process for the preparation of a compound of the formula (II) defined in claim 12 further comprising the step of: reacting the compound of the formula (II), wherein $R^1$ and $R^2$ are as defined above, with a compound of the formula (VIII)

or its salt wherein:
$R^4$ is an optionally substituted alkyl;
$R^5$ is hydrogen or alkyl or the radical of the formula (VII) constituted by $R^4$, $R^5$ and the carbon and nitrogen atoms attached thereto in the formula (III)

is part of any of the ring systems (A), (B), (C), (D), (E), (F), (G), (H), (I) or (J) listed below, and and $R^6$ is hydrogen, alkyl or aralkyl,
to obtain a compound of the Formula (III):

or a pharmaceutically acceptable salt thereof, wherein $R^1$, $R^2$, $R^4$, $R^5$ and $R^6$ are as defined above;

and if desired, converting the ester of the formula (III) thus obtained wherein $R^6$ is alkyl or aralkyl, into the corresponding carboxylic acid of the formula (III), wherein $R^6$ is hydrogen; and if desired, transforming a compound of the formula (III) obtained into its salt.

25. The process for the preparation of a compound of the formula (II) defined in claim 24 in which a compound of the Formula (II) is converted into the compound of the Formula (III), namely, ramipril, wherein $R^1$ is phenyl, $R^2$ is ethyl, $R^6$ is hydrogen) and the radical of the formula (VII) in the formula (III) is the group of the formula (C), by reacting the compound of the formula (II) with (S,S,S)-2-azabicyclo[3.3.0]octane-3-carboxylic acid benzylester or its salt, and removing the benzyl group by catalytic hydrogenation.

26. The process for the preparation of a compound of the formula (II), defined in claim 24 in which the compound of the Formula (II) is converted into a compound of the Formula (III), namely, perindopril, wherein $R^1$ is methyl, $R^2$ is ethyl, $R^6$ is hydrogen) and the radical of the formula (VII) in the formula (III) is the group of the formula (B), by reacting the compound of the formula (II) with (S,S,S)-perhydroindole-2-carboxylic acid benzylester or its salt, and removing the benzyl group by catalytic hydrogenation.

* * * * *